US012303296B2

(12) United States Patent
Othmane et al.

(10) Patent No.: US 12,303,296 B2
(45) Date of Patent: May 20, 2025

(54) SYSTEM AND METHOD FOR CONTROLLING PHYSICAL SYSTEMS USING BRAIN WAVES

(71) Applicants: Lotfi B. Othmane, Ames, IA (US); Nicholas J. Schmidt, New Brighton, MN (US)

(72) Inventors: Lotfi B. Othmane, Ames, IA (US); Nicholas J. Schmidt, New Brighton, MN (US)

(73) Assignee: Iowa State University Research Foundation, Inc., Ames, IA (US)

( * ) Notice: Subject to any disclaimer, the term of this patent is extended or adjusted under 35 U.S.C. 154(b) by 764 days.

(21) Appl. No.: 17/353,396

(22) Filed: Jun. 21, 2021

(65) Prior Publication Data
US 2022/0401004 A1 Dec. 22, 2022

(51) Int. Cl.
*A61B 5/369* (2021.01)
*A61B 5/00* (2006.01)
(Continued)

(52) U.S. Cl.
CPC .......... *A61B 5/7246* (2013.01); *A61B 5/6803* (2013.01); *A61B 5/7257* (2013.01);
(Continued)

(58) Field of Classification Search
CPC ... A61B 5/7246; A61B 5/6803; A61B 5/7257; A61B 5/7267; A61B 5/7264;
(Continued)

(56) References Cited

U.S. PATENT DOCUMENTS

| 7,162,295 B2 * | 1/2007 | Ryu ...................... G06F 3/015 |
| | | 600/545 |
| D565,735 S | 4/2008 | Washbon |

(Continued)

FOREIGN PATENT DOCUMENTS

| EM | 0007346600001 S | 9/2007 |
| EM | 0009866170001 S | 11/2008 |

(Continued)

OTHER PUBLICATIONS

Diaz, Alejandro. "Videogame control through EEG (part 2)." *Medium*, Nov. 20, 2018, Retrieved Nov. 29, 2020. https://medium.com/@alejandrodiazillo/videogame-control-through-eeg-part-2-73e8c3391fee.

(Continued)

*Primary Examiner* — Navin Natnithithadha
(74) *Attorney, Agent, or Firm* — Reinhart Boerner Van Deuren P.C.

(57) ABSTRACT

Embodiments of a system for controlling an object using brainwaves are disclosed. The system includes a set of EEG electrodes configured to be positioned on a head of a user and to collect EEG signals. The system further includes one or more computer readable storage mediums storing a framework configured to execute an extensible architecture through which EEG signals are interpreted for control of the object. The framework includes an EEG device plugin associated with the set of EEG electrodes and configured to extract the EEG signals from the set of EEG electrodes. The framework also includes an interpreter plugin configured to convert the EEG signals extracted by the EEG device plugin into a command. Further, the framework includes an object control plugin configured to access the command through an extension point of the interpreter plugin and to execute the command to control the object.

15 Claims, 3 Drawing Sheets

(51) Int. Cl.
*A61B 5/31* (2021.01)
*G06F 3/01* (2006.01)
*G06N 3/02* (2006.01)
*G06N 3/06* (2006.01)
*G06N 3/08* (2023.01)
*G16H 50/00* (2018.01)

(52) U.S. Cl.
CPC .............. *A61B 5/7267* (2013.01); *A61B 5/31* (2021.01); *A61B 5/369* (2021.01); *A61B 5/7264* (2013.01); *A61B 2560/02* (2013.01); *G06F 3/015* (2013.01); *G06N 3/02* (2013.01); *G06N 3/06* (2013.01); *G06N 3/08* (2013.01); *G16H 50/00* (2018.01)

(58) Field of Classification Search
CPC ..... A61B 2560/02; A61B 5/744; A61B 5/374; A61B 5/7475; A61B 5/384; G06F 3/015; G06N 3/02; G06N 3/06; G06N 3/08; G16H 50/00
USPC .................................................. 600/544, 545
See application file for complete search history.

(56) References Cited

U.S. PATENT DOCUMENTS

| | | | |
|---|---|---|---|
| 7,865,235 B2 | 1/2011 | Le et al. | |
| 8,326,408 B2* | 12/2012 | Green | A61B 5/7246 |
| | | | 600/545 |
| 8,396,546 B2* | 3/2013 | Hirata | A61B 5/318 |
| | | | 600/545 |
| 8,989,835 B2* | 3/2015 | Badower | A61B 5/369 |
| | | | 600/383 |
| 9,020,587 B2* | 4/2015 | Green | A61B 5/375 |
| | | | 600/545 |
| 9,060,671 B2* | 6/2015 | Badower | A61B 5/7203 |
| 9,215,978 B2* | 12/2015 | Knight | A61B 5/7203 |
| 9,472,207 B2 | 10/2016 | Gondi et al. | |
| 9,622,660 B2 | 4/2017 | Le et al. | |
| 9,717,440 B2 | 8/2017 | Abdelghani et al. | |
| 9,730,597 B2* | 8/2017 | Green | A61B 5/4851 |
| 9,763,592 B2 | 9/2017 | Le et al. | |
| 9,864,431 B2 | 1/2018 | Keskin et al. | |
| 9,867,548 B2 | 1/2018 | Le et al. | |
| 9,907,482 B2* | 3/2018 | Knight | A61B 5/369 |
| 10,028,703 B2 | 7/2018 | Le et al. | |
| 10,108,264 B2 | 10/2018 | Le et al. | |
| 10,194,865 B2 | 2/2019 | Le et al. | |
| 10,291,977 B2 | 5/2019 | Mackellar et al. | |
| 10,592,001 B2 | 3/2020 | Berenzweig et al. | |
| 10,779,745 B2* | 9/2020 | Knight | A61B 5/165 |
| 10,795,441 B2 | 10/2020 | Lee et al. | |
| 10,842,403 B2* | 11/2020 | Badower | A61B 5/6803 |
| 11,704,790 B2* | 7/2023 | Leuthardt | G06V 10/764 |
| | | | 600/408 |
| 11,980,469 B2* | 5/2024 | Knight | A61B 5/0006 |
| 2005/0137493 A1* | 6/2005 | Ryu | G06F 3/015 |
| | | | 600/544 |
| 2007/0060830 A1 | 3/2007 | Le et al. | |
| 2007/0060831 A1 | 3/2007 | Le et al. | |
| 2007/0066914 A1 | 3/2007 | Le et al. | |
| 2007/0173733 A1 | 7/2007 | Le et al. | |
| 2007/0179396 A1 | 8/2007 | Le et al. | |
| 2007/0225585 A1 | 9/2007 | Washbon et al. | |
| 2007/0235716 A1 | 10/2007 | Delic et al. | |
| 2007/0238945 A1 | 10/2007 | Delic et al. | |
| 2008/0159365 A1 | 7/2008 | Dubocanin et al. | |
| 2008/0211768 A1 | 9/2008 | Breen et al. | |
| 2008/0218472 A1 | 9/2008 | Breen et al. | |
| 2009/0105576 A1 | 4/2009 | Do et al. | |
| 2009/0259137 A1 | 10/2009 | Delic et al. | |
| 2009/0318826 A1* | 12/2009 | Green | A61B 5/742 |
| | | | 600/545 |
| 2011/0218453 A1* | 9/2011 | Hirata | A61B 5/7267 |
| | | | 600/544 |
| 2013/0035579 A1 | 2/2013 | Le et al. | |
| 2013/0218044 A1* | 8/2013 | Green | G06F 3/015 |
| | | | 600/545 |
| 2013/0314243 A1 | 11/2013 | Le | |
| 2013/0317382 A1 | 11/2013 | Le | |
| 2013/0317384 A1 | 11/2013 | Le | |
| 2015/0227199 A1* | 8/2015 | Green | G06F 3/015 |
| | | | 345/156 |
| 2015/0238105 A1* | 8/2015 | Green | A61B 5/742 |
| | | | 600/545 |
| 2015/0379628 A1 | 12/2015 | Yu | |
| 2016/0029958 A1 | 2/2016 | Le et al. | |
| 2016/0029959 A1 | 2/2016 | Le et al. | |
| 2016/0259492 A1 | 9/2016 | Le et al. | |
| 2017/0027517 A9 | 2/2017 | Le et al. | |
| 2017/0041699 A1 | 2/2017 | Mackellar et al. | |
| 2017/0303854 A9 | 10/2017 | Le et al. | |
| 2017/0347907 A1 | 12/2017 | Le et al. | |
| 2018/0092558 A1 | 4/2018 | Le et al. | |
| 2018/0096336 A1 | 4/2018 | Yu et al. | |
| 2018/0317794 A1 | 11/2018 | Mackellar et al. | |
| 2019/0018488 A1 | 1/2019 | Le et al. | |
| 2019/0090749 A1* | 3/2019 | Leuthardt | G16H 30/40 |
| 2019/0117158 A1 | 4/2019 | Le et al. | |
| 2019/0222918 A1 | 7/2019 | Mackellar et al. | |
| 2019/0246982 A1 | 8/2019 | Mackellar et al. | |
| 2019/0294243 A1 | 9/2019 | Laszlo et al. | |
| 2019/0320979 A1 | 10/2019 | Le et al. | |
| 2019/0336030 A1 | 11/2019 | Le et al. | |
| 2019/0384392 A1 | 12/2019 | Aimone et al. | |
| 2020/0057498 A1* | 2/2020 | Artemiadis | G06N 20/00 |
| 2020/0333882 A1 | 10/2020 | Mallinson | |
| 2023/0306595 A1* | 9/2023 | Leuthardt | A61B 34/10 |

FOREIGN PATENT DOCUMENTS

| | | |
|---|---|---|
| TW | 200835466 A | 9/2008 |
| WO | WO 2003/073175 A2 | 9/2003 |
| WO | WO 2008/109694 A1 | 9/2008 |
| WO | WO 2008/109699 A2 | 9/2008 |
| WO | WO 2009/087486 A2 | 7/2009 |
| WO | WO 2019/092456 A1 | 5/2019 |
| WO | WO 2020/069181 A1 | 4/2020 |
| WO | WO 2020/148931 A1 | 7/2020 |

OTHER PUBLICATIONS

Gatti, Prajwal. "EEG Controlled Rover—A Brain-Computer Interface." *Hackernoon*, Aug. 15, 2018, Retrieved Nov. 29, 2020. https://hackernoon.com/mind-controlled-rover-2f43bcfe8eb6.

Rosca et al. "Design of a Brain-Controlled Video Game based on a BCI System." *MATEC Web Conference 290*, 2019, Retrieved Nov. 29, 2020, pp. 1-9. DOI: https://doi.org/10.1051/matecconf/201929001019.

Schmidt, Nick. "Control of Physical Objects Utilizing Brain Computer Interfaces." *Creative Components—Master Thesis*, Iowa State University, Ames, IA., 2020, pp. 1-54.

* cited by examiner

SYSTEM AND METHOD FOR CONTROLLING PHYSICAL SYSTEMS USING BRAIN WAVES

FIELD OF THE INVENTION

This invention generally relates to a brain computer interface and in particular to a brain computer interface having an extensible architecture through which plugins provide compatibility for a wide variety of electroencephalogram (EEG) devices and usability for developers without experience using brain computer interfaces.

BACKGROUND OF THE INVENTION

There are relatively few commercially available consumer brain computer interfaces (BCI), especially outside of those geared to medical use. Only a few commercial products are available that target BCI for application control. However, these products are limited in one way or another.

For example, Emotiv and Neurosky provide a range of products that include a headset to extract brain data and software to utilize it. Devices, such as those available from Emotiv or Neurosky, typically operate with proprietary software. As such, there is no way to develop for a general hardware device, and any piece of software would have to develop specifically for that brand of hardware device.

Additionally, open source software providers, such as OpenBCI, provide software packages and libraries that allow for interfacing with general hardware devices. For example, these open source software providers are compatible with DIY devices (e.g., using an Arduino board) or generic brain data capture devices. This allows for a more open environment than the offerings from Emotiv or NeuroSky, but there are still compatibility issues with devices that do not implement the OpenBCI libraries.

OpenVIBE seeks to solve the compatibility issue by implementing a GUI coding interface with pre-made blocks which handle various operations. Users can implement their own "boxes" using either python or C++. This allows for developers to create their own logical flow for a BCI device and tie it into their own software. However, one of the major pitfalls of OpenVIBE is its use of a graphical coding interface and a relatively complex method of coding support outside of the GUI. The use of a graphical coding interface requires that developers learn to use this GUI and brings developers outside of their own environment. This can be an issue for some development projects where developers would prefer that the solution be included in their own software. Additionally, a developer must understand the API and flow of data of the BCI device in order to develop the core implementation of the software utilizing the GUI.

OpenBCI devices cannot easily work with NeuroSky or Emotiv devices, and NeuroSky and Emotiv devices require coding specifically for their devices. Further, OpenVIBE requires a complex understanding of the flow of a BCI to implement. Additionally, to easily work with OpenVIBE a developer must move outside of their environment and work within the OpenVIBE GUI code editor.

As such, the field of BCI lacks a unified platform, which limits the capability for large scale development of BCI capable applications and devices. In order for BCI software to progress, a platform must exist which is capable of controlling physical and digital devices and which can be easily expanded.

BRIEF SUMMARY OF THE INVENTION

Embodiments of the present disclosure provide a BCI software platform that allows a developer to program in a chosen language without requiring a deep understanding of brain data interpretation and brain control theory. Instead, a developer just needs to incorporate a plugin that invokes brain data extraction and training of the presently disclosed BCI. These and other advantages of the invention, as well as additional inventive features, will be apparent from the description of the invention provided herein.

In one aspect, the embodiments of the present disclosure provide a system for controlling an object using brainwaves are disclosed. The system includes a set of electroencephalogram (EEG) electrodes configured to be positioned on a head of a user and to collect EEG signals. The system further includes one or more computer readable storage mediums storing a framework configured to execute an extensible architecture through which EEG signals are interpreted for control of the object. The framework includes an EEG device plugin associated with the set of EEG electrodes and configured to extract the EEG signals from the set of EEG electrodes. The framework also includes an interpreter plugin configured to convert the EEG signals extracted by the EEG device plugin into a command. Further, the framework includes an object control plugin configured to access the command through an extension point of the interpreter plugin and to execute the command to control the object. The extensible architecture is configured to extend to at least one further EEG device plugin associated with a different set of EEG electrodes and to at least one further object control plugin associated with at least one further set of commands and at least one further object.

According to another aspect, embodiments of the present disclosure provide a method of controlling objects using brainwaves. In the method, electroencephalogram (EEG) signals are collected from a first set of EEG electrodes positioned on a head of a user. The EEG signals are extracted from the first set of EEG electrodes using a first EEG device plugin associated with the first set of EEG electrodes. The EEG signals extracted by the first EEG device plugin are converted into a first set of commands using an interpreter plugin. The first set of commands are accessed by a first object control plugin through an extension point of the interpreter plugin, and the first set of commands is executed using the first object control plugin to control the first object. In the method, the first EEG device plugin, the interpreter plugin, and the first object control plugin are part of a framework defining an extensible architecture. The extensible architecture is configured to extend to at least one further EEG device plugin associated with a different set of EEG electrodes and to at least one further object control plugin associated with at least one further set of commands and at least one further object.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

According to embodiments of the present disclosure, a framework for using brainwaves to control a set of extensible physical objects as well as related methods are disclosed herein. Using the disclosed framework, brainwave sensors are used to measure electrical signals from the brain of a user. The measurements are used to generate reference models representing the brainwaves of a given user associated with their intent to execute each of the commands on the physical objects of interest. Thus, in the framework, a user's commands are inferred from their brain signals, and the commands are executed on the appropriate physical objects. The framework supports adding and modifying applications that control the physical object at run time without requiring a deep knowledge of brainwaves by allowing application developers to simply incorporate plugins that tap into the control functionality of the framework. These and other aspects and advantages will be described in relation to the embodiments discussed below and shown in the figures. The embodiments presented herein should be considered illustrative, not limiting, on the scope of the disclosure.

Figure 1:
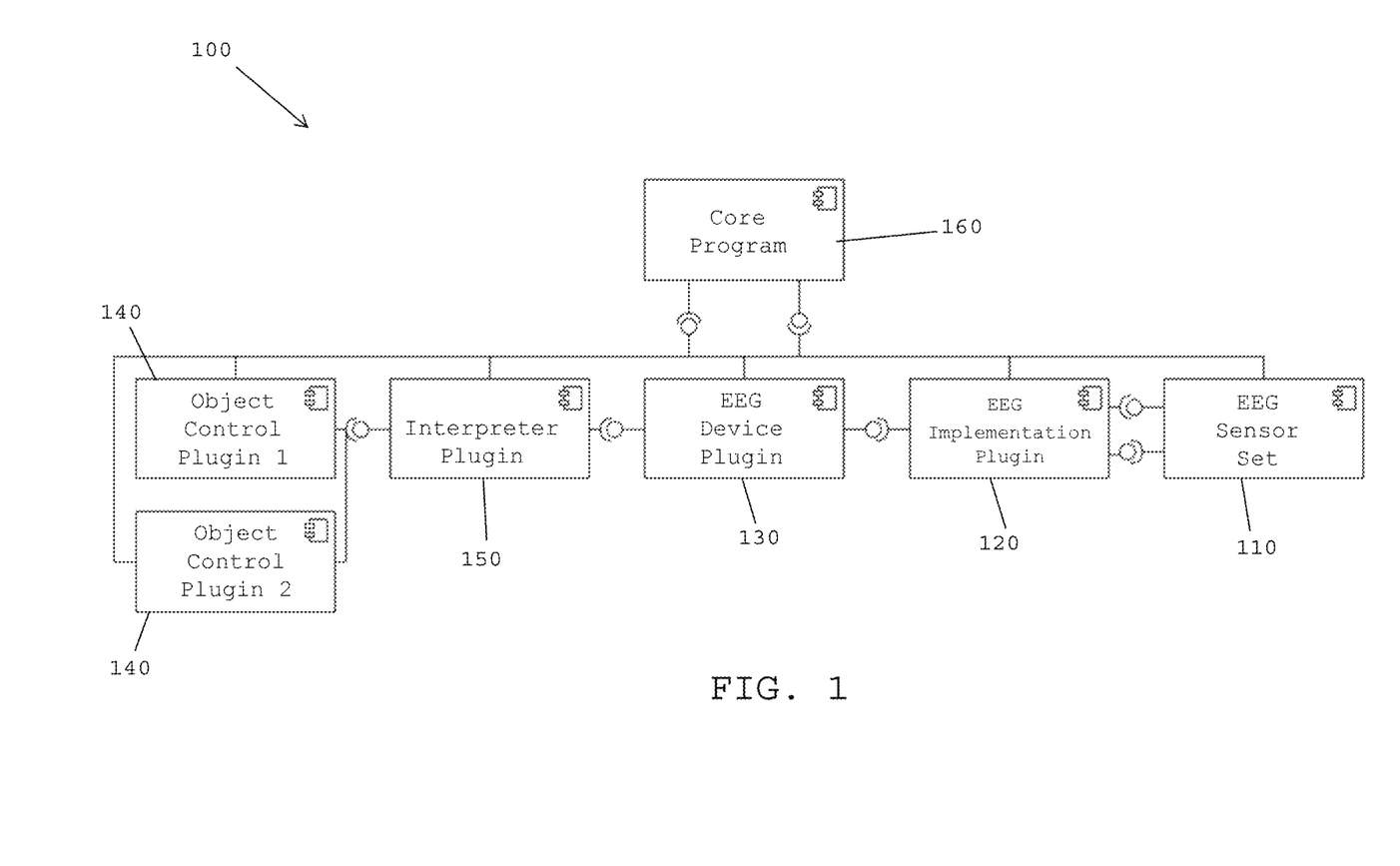
FIG. 1 depicts a brain computer interface for controlling objects using an extensible framework, according to exemplary embodiments.

FIG. 1 depicts a schematic representation of a framework 100 of an extensible architecture for brainwave control of a physical object. Through the framework 100, brainwave activity is captured using an electroencephalogram (EEG) sensor set 110. The EEG sensor set 110 includes a plurality of EEG electrodes configured to be positioned at various locations on a user's head. These electrodes measure minute voltages generated within the brain in microvolts. The EEG sensor set 110 can utilize any number of electrodes with a higher number of electrodes allowing for a more accurate signal placement. For example, many commercially available products provide from five to thirty-two electrodes per EEG sensor set 110. Advantageously, EEG electrodes are relatively inexpensive and easy to use in comparison to other methods of reading brain activity (such as MRI). Further, EEG electrodes simply read voltages at their location, allowing for near-instant recording of data that is easily analyzable. While EEG signals can be prone to muscle interference between the electrode and region of the brain sensed and are difficult to place at precise locations of the brain because of physiological differences between individuals, EEG electrodes can still differentiate signal groupings, allowing for development of unique signal patterns.

Often, the EEG electrodes are provided as part of a headset or cap, which allows the EEG electrodes to be repeatably and accurately positioned on the user's head. As will be appreciated from the following discussion, one advantage of the present disclosure is that any of a variety of commercially available headsets or other EEG sensor sets are able to be used in the framework 100.

In the framework 100, the sensor data is captured from the EEG sensor set 110 and interpreted using an EEG implementation 120. In embodiments, the EEG implementation 120 is, for example, an application programming interface (API). The EEG implementation 120 communicates with an EEG device plugin 130. According to the present disclosure the plugin is a bundle that adds functionality to an application through defined architecture for extensibility. Advantageously, the plugin architectures allows third-party developers to build applications that are modular, customizable, and extensible. In embodiments, the EEG device plugin 130 utilizes a software development kit (SDK) of a given EEG implementation 120 to access the EEG data. For example, Emotiv EPOC+ is a commercially available EEG sensor set 110 incorporated into a headset. This device operates in conjunction with an EEG implementation having an API to extract the EEG signals generated by the EEG sensor set 110. Other commercially available EEG sensor sets 110 similarly operate with various proprietary or open source implementations and API to which access is provided in an SDK. In general, each different EEG sensor set 110 in the framework 100 will need its own particular EEG device plugin 130.

The EEG device plugin 130 communicates with object control plugins 140 via an interpreter plugin 150. The object control plugins 140 are devices or applications that utilize brainwave commands for control of physical objects. For example, a simple maze chase video game application may need commands for up, down, left, and right for a user's avatar to navigate the maze. The interpreter plugin 150 translates the EEG signals from the EEG device plugin 130 to supply the four directional commands needed by the object control plugin 140. In another example, the object control plugin 140 is a light fixture having on and off commands to control the light fixture. The interpreter plugin 150, in this case, translates the EEG signals from the EEG device plugin 130 to supply the on/off commands needed for this example of the object control plugin 140.

In order to translate the EEG signals into commands, the framework 100 includes a core program 160 that provides a training module for training a user on the commands. For example, a user is able to train using the training module of the core program 160 for a variety of commands. Training will be discussed more fully below, but for the present discussion, a user with an EEG sensor set 110 practices commands, such as up, down, left, right, on, or off, until a pattern in brain activity is recognized from the EEG signals captured by the EEG sensor set 110. These EEG signals are extracted through the EEG implementation 120, and the EEG plugin 130 provides the interface to interact with the core program 160 for training and with the object control plugin 140 to issue commands.

To conduct the training, the core program 160 of the framework 100 implements machine learning algorithms that recognizes the user's intent on physical objects and acts on the objects accordingly. The core program 160 includes a training module to generate a machine learning model that links the users' EEG signals to their intents on the given physical object. To accomplish the this training, the EEG signals are transformed to the frequency domain, and the measurements are used as input to a machine learning algorithm to train a reference model that associates the signals with the set of commands for the physical object.

To create more consistent readings for the purposes of training and eventual commands, the EEG signals are transformed into brainwaves in embodiments. Brainwaves can be divided into Delta, Theta, Alpha, Beta, and Gamma brainwaves. Delta waves consist of waves which are of the frequency 0.5-4 Hz. These very low frequency brainwaves are often associated with meditation or dreamless sleep.

Theta waves are those waves which range from 5-8 Hz and are often associated with drowsiness or dreaming. Alpha brain waves are those waves which range from 9-14 Hz and are often associated with a relaxed or resting brain. Beta brain waves are those brainwaves that range from 15-30 Hz and are often associated with an alert or working brain. Finally, Gamma waves are all other waves and are associated with a highly active brain.

The concept of a power band is used to measure the prevalence of different brainwaves. This concept essentially measures the prevalence of each type of wave within the brain. This operation utilizes the spectral density operation, which calculates the amount of power each frequency range is expected to contribute to the overall range of frequencies.

In embodiments, the EEG signals are converted to the frequency domain and interpreted using a Fast Fourier Transform (FFT). Advantageously, FFT is computationally lighter than other methods, such as auto-regressive methods and wavelet transforms. While FFT is more susceptible to noise, has issues interpreting quick changes in data, and requires a large number of signals to identify it, the FFT advantageously does not require the heavy computation or modeling, and the frequency resolution is high enough to allow for pattern matching in the presently disclosed BCI architecture.

In embodiments, the EEG data is converted to power band data utilizing an FFT. Algorithm 1, provided below, describes a method for this conversion. As mentioned, performing an FFT requires a large number of samples, and in Algorithm 1, 256 samples were utilized. Further, in Algorithm 1, noise is removed from the data. In embodiments, noise is removed with a Hann window and a detrend method. These functions will emphasize the major points of the wave and remove smaller ripples near the outsides of the waveform. Further, according to Algorithm 1, the data is squared to retrieve the power band data. Then, in Algorithm 1, the data is iterated over the frequencies, and the waves are added to the correct band.

```
Algorithm 1: Power band Conversion
Result: Power Band Data by Bucket
EEGData = new Arrary;
while Receiving Data do
    EEGData.insert(Data);
    if length(EEGData) = 256 then
        Detrend(EEGData);
        Hanning(EEGData);
        FFT(EEGData);
        PowerDensity = FFT*FFT;
        for Frequencies in PowerDensity do
            Add frequency to corresponding power band bucket;
        end
        Print Bucket information to a log file;
        EEGData.remove(Oldest 16);
    end
end
```

In embodiments, the obtained brainwave data was analyzed using complex neural nets and deep learning. In such embodiments, the neural network has the capability of finding non-linear relationships between inputs and outputs. While such neural networks require a large dataset, the required volume of data is able to be recorded through most commercially available EEG sensor sets 110. For example, Emotiv Epoc+ takes 2048 readings per second, which are provided to the user at a rate of 128 or 256 samples per second, which allows for rapid generation of the data necessary for implementing the neural network.

Figure 2:
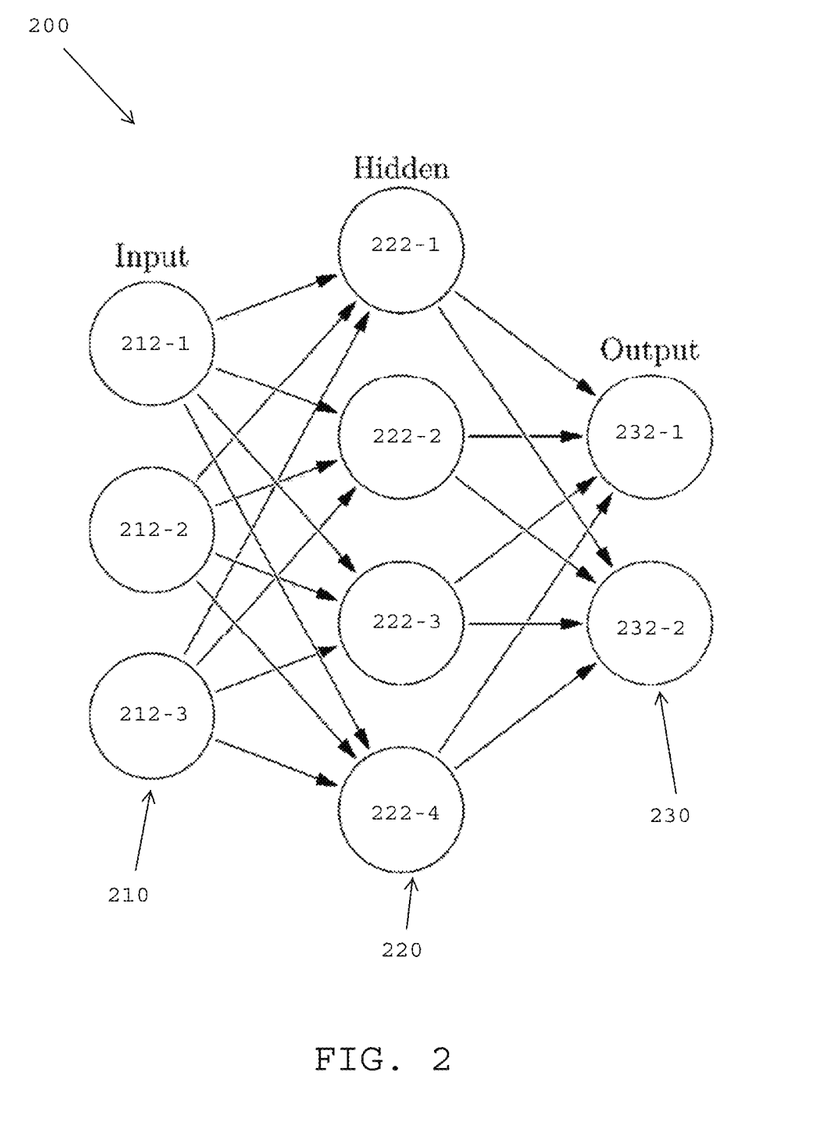
FIG. 2 depicts a simplified schematic of a neural network configured to learn or recognize commands from brainwaves, according to exemplary embodiments.

In the presently disclosed examples, Keras was utilized to perform the neural network deep learning. Keras is an open-source software that utilizes tensor flow to leverage a graphics card's computation power for the categorization of commands. FIG. 2 depicts a simplified neural network 200 that can be used for deep learning. The neural network 200 includes an input layer 210 with each node 212-1, 212-2, . . . 212-n to correspond to each input signal. While the simplified schematic of FIG. 2 depicts three nodes, 212-1, 212-2, 212-3, the presently disclosed examples used 70 input nodes, corresponding to the five brainwave frequencies in the power-band data for each of the 14 data recording electrodes in the EEG sensor set 110 used in the example embodiments.

In the neural network 200, the data from the input layer 210 is passed into hidden layers 220 within the neural network 200. In the simplified schematic of FIG. 2, the neural network 200 only includes a single hidden layer 220. The hidden layers 220 each hold a predefined number of nodes 222-1, 222-2, . . . 222-n. In the simplified schematic of FIG. 2, the single hidden layer 220 includes four nodes 222-1, 222-2, 222-3, 222-4. During training, these hidden layers 220 continually reconnect with nodes 222-1, 222-2, . . . 222-n of different hidden layers 220 and with nodes 222-1, 222-2, . . . 222-n within their own layer 220. Each hidden node 222-1, 222-2, . . . 222-n continually adjusts its parameters to formulate the requirements for when the node 222-1, 222-2, . . . 222-n should activate. This is determined based upon the connections with previous nodes as well as a weight which is assigned to these connections to determine how important they are in the final determination. This process is repeated many times over the pre-classified test data until the model goes through the preset amount of iterations.

After passing through the hidden layers 220, an output is arrived at in the output layer 230. The output layer 230 corresponds to the potential recognized commands (e.g., up, down, left, right, on, off in the examples discussed above). In the simplified schematic of FIG. 2, the output layer 230 includes two nodes 232-1, 232-2 but could include many more nodes 232-1, 232-2, . . . 232-n depending on the number of outcomes for a given application.

In the presently disclosed examples, the neural network 200 was developed with one input layer 210, two hidden layers 220, and one output layer 230.

To test the machine learning methodology in real time, a relatively simple program was developed to control a lamp utilizing EEG signals. The lamp was connected to a Raspberry Pi running a local webserver, and the webserver was configured to listen on the localhost for a command sent from the computer running the EEG software. The webserver was configured to toggle a relay to enable electrical signal to flow to the lamp. The following process was used to train for control of the lamp:
  1. Record five to ten second long logs containing the raw EEG data for sending no command (neutral)
  2. Record five ten second long logs containing the raw EEG data for sending a lamp toggle command (toggle)
  3. Convert these logs into power band data using the FFT algorithm (Algorithm 1)
  4. Train a model in Keras using the described method
  5. Import this trained model into the interpreter, a program that listens to EEG data and utilizes the model to determine when a command is sent In order to accomplish the final step, an algorithm, Algorithm 2 (below) was developed to work with the live data. This algorithm works similarly to the power band data but adds additional steps for working with the live data and for the categorization step.

---

Algorithm 2: Command Interpretation
Result: Command
import keras model;
while Receiving Data do
    EEGData.insert(Data);
    if length(EEGData) = 256 then
        Detrend(EEGData);
        Hanning(EEGData);
        FFT(EEGData);
        PowerDensity = FFT*FFT;
        for Frequencies in PowerDensity do
            Add frequency to corresponding power band bucket;
        end
        keras.predict(PowerDensity);
        EEGData.remove(Oldest 16);
    end
end

---

This categorization algorithm worked for controlling the lamp (toggle on/off), and the level of accuracy was also suitable for controlling an avatar in a maze chase game. The maze chase game was retrieved from an open source arcade machine emulator (MAME). A virtual joystick driver (Vjoy) was utilized to enable a non-joystick device to control the joystick game. To implement using python programming, Pyvjoy, which contains a python library for interaction with Vjoy, was also utilized. A model trained for four inputs (four nodes 212-1, 212-2, 212-3, 212-4 in input layer 210) was also required, one for each joystick direction. It was found that, using the presently disclosed framework 100, the maze chase game could be controlled at the same time as the lighting program.

Having described the framework 100 and its various components and demonstrated the operability thereof, the following discussion focuses on the manner in which the components interface. As discussed above, the interface is intended to work with any or most commercially available headsets and to allow developers to program applications in their chose programming language without needing any specialized knowledge of deep learning or brainwave interpretation. In general, the architecture of the framework can be described as a plugin architecture, but specialized plugins needed to be developed in order to provide the level of modifiability and extensibility desired to accomplish the stated goals.

A plugin architecture is an architecture whose core functionality can be expanded or modified based on the insertion of new classes or objects. These classes or objects must fit a predefined definition for the structure of the plugin. These are dependent upon the software being expanded, but usually involve some type of scripting language and .XML configuration file.

According to certain aspects, the plugins work by utilizing "hooks" that provide predefined areas which allow for user defined code to run. A plugin developer writes code to access a piece of software when a particular hook happens. Another type of plugin is an extension point. Extension points are defined within each individual plugin through the use of an .XML file. This file lays out the required fields which an extending plugin must implement, as well as the format of any data that will be transferred between the two. This is typically implemented as a Java class which can then be used to call specific needed methods. The plugins themselves are then defined within .XML files which describe some basic information about the plugin. The implementation of these plugins is then completed using a Java class. Through extension points, a developer can easily add any plugins onto the provided extension points and allow for complex interaction between plugins, allowing for a high level of customization and modification of the available functionalities for the software.

According to the present disclosure, the core of the framework 100 architecture is defined based on an extension-type architecture and hook-type plugins drive the rest of the application. Using this hybrid architecture, two new types of plugins were developed for the framework 100: the device plugin (EEG device plugin 130) and the interface plugin. The device plugin 130 is responsible for communicating with the EEG sensor set 110. The devices have a generic interface. Interface plugins connect to these generic hooks within the device plugins and wait for input. Generic plugins act based upon any interfaces which they extend. It should be noted that embodiments of the generic plugin disclosed here are illustrative in nature, and the specific actions described therein are not considered "generic." That is, "generic" refers to the structure of the plugin and not the specific contents of the plugin, which will be different for various different applications. With respect to the lighting example provided in Table 1, below, the generic plugin contains actions in each element associated with controlling a light, which will be different when controlling a different object.

A plugin file includes any required functionality for the core of a plugin. Logic related to specific extension points are placed into extension point implementation files. A plugin implementation may contain no functionality so that these functionalities can be passed off to extension points. These extension points as well as any extensions implemented by the plugin are defined within the plugin definition file.

A plugin definition file defines the details of a plugin. An example of this file is included in Table 1. The file begins with enclosing plugin tags to allow for parsing by the core program 160. The plugin then identifies some basic facts about itself including, for example, its name, id, what type of plugin it is, the plugin version, and the developer.

TABLE 1

Generic Plugin Definition for Controlling a Light

```
<plugin
name = "Pi"
id = "lighting.pi"
type = "logical"
version = "1.0"
developer = "Smith, John"
<extension id = "interpretor.interpretor.command">
    <actionSet
      setName = "light Controls"
      setDescription = "A set of actions to control a light switch through a
```

TABLE 1-continued

Generic Plugin Definition for Controlling a Light

```
connection to a raspberry PI"
      setModel = "Lighting.json"
      setWeights = "Lighting.h5">
      <commandAction
         actionName = "toggleLight"
         actionDescription = "Toggles the light using the PI"
         commandNumber = "1"
         commandTimer = "15"
         class = "lightToggle">
      </commandAction>
    </actionSet>
</extension>
<extension-point id = "lighting.pi.example" name = "example" schema = example"/>
</plugin>
```

The next portion of the plugin definition file is the extension list. Each extension point extended by this plugin must be defined within the extension tags. To begin an extension, the id of the extension point must be entered. Next, any additional elements required by the extension point must be enclosed within their own tags. In the example from Table 1, there are two elements required by the extension point interpreter.interpreter.command. Within each tag, an extension point's elements must be passed the required variables. For example, in the actionSet element, the variables setName, setDescription, setModel, and setWeights are passed. The actionSet element is also passed a different element, known as commandAction. This commandAction element is given the variables actionName, action-Description, commandNumber, commandTimer, and a class which implements the required interface.

The final requirement within a generic plug-in definition file is the inclusion of any extension points. The plugin provided in Table 1 does not have any extension points built into its functionality, so an example extension point was created. To declare an extension point, the extension-point tag is used. This definition must include an ID for the extension point, as well as a name and a schema. This schema points to the file which holds the definition for that extension point.

The developed architecture also implements a form of extension points. These extension points are defined by each plugin within an extension point schema file (.ext). An extension point schema file for the extension point referenced by Table 1 is available in Table 2. Similar to the plugin definition file, this extension point file begins with a schema tag to allow for the core program to parse it. The next tag is an element tag. This defines the elements that can be implemented by any plugin wishing to extend this point. The first element in any extension point is the extension tag. This tag lists which elements must be implemented by default. In this example, any extension wishing to extend out the extension point must include at least one actionSet element.

TABLE 2

Extension Point Definition

```
<schema>
    <element name = "extension">
       <required>
          <elementReq ref = "actionSet" min = "1" max = "0"/>
       </required>
    </element>
    <element name = "actionSet" implementation = "actionSet">
       <required>
          <elementReq ref = "commandAction" min = "1" max = "0"/>
       </required>
       <argument name = "setName" type ="str" req = "yes"></argument>
       <argument name = "setDescription" type = "str" req "no"> </argument>
       <argument name = "setModel" type = "str" req = "yes"></argument>
       <argument name = "setWeights" type = "str" req = "yes"></argument>
       <argument name = "class" type = "string" req = "no"></argument>
    </element>
    <element name = "commandAction" implementation = "commandAction">
       <argument name = "actionName" type ="str" req = "yes"></argument>
       <argument name = "actionDescription" type = "str" req "no"> </argument>
       <argument name = "commandNumber" type ="str" req = "yes"></argument>
       <argument name = "commandTimer" type = "int" req = "yes"></argument>
       <argument name = "class" type ="string" req = "no"></argument>
    </element>
</schema>
```

Next, a second element is listed. This is the required actionSet element. This actionSet requires the use of a commandAction element and also requires several arguments. The argument tag defines these arguments name and type, as well as whether they are required. A similar definition is created for the commandAction element, but as can be seen from Table 2, there are no required elements for a commandAction.

The next part of an extension point is the extension point implementation file. For many plugins, this is where a majority of the functionality will go. This file must have the same name as the extension definition file and contains the python code for this extension point. This code will execute based on the methodology implemented by the developer. It is possible for an extending plugin to cause the extension point to take action but it is also possible for an extension point to cause its extensions to take action. Each extension point must also implement an extensionHandler( ) method. This method will be called as the generic communication method between an extension point and its extension, performing the implemented behavior for each extension.

The final parts of an extension point are the element implementation files. These files can range in usability. Some definition files may contain nothing but the expected methods that an element must implement and pass the functionality to the extension point. Other elements may be fully implemented and function based solely on the attributes passed into the extension point from an extending plugin. These decisions are left up to the plugin developer.

Having described a generic plugin and extension point, the device plugin 130 is now described. This type of plugin was created specifically for working in the context of a BCI. The device plugin definition is divided into two parts. The first is the creation of a type that holds the extension point definition for all devices which utilize this type. This forces consistency across all implementations of this type. For example, a new EEG headset could be used with the software and no changes would have to be made to other plugins in the architecture. An example type definition provided in Table 3, below. This definition must include the name, the type, the version, the developer, and a schema describing the extension point definition. Additionally, the type can include required arguments for an interface wishing to access the device. As can be seen from the "nodes" requirement, these requirements can be setup as identifiers with the ident argument. A requirement set as an identifier can be used by an interface to select a device with a requirement whose argument matches their passed arguments.

The second part of defining a device plugin is through the EEG implementation 120, i.e., where the specific code for each device is implemented. For the Emotiv headset used in the examples, this implementation contains all information about how the Emotiv headset runs. Each device implementation 120 must include a run method which will execute for the device within its own thread. The Emotiv implementation will continually collect data and pass it off through the extension point, which has been forced to be the generic EEG extension due to its implementation as a device.

TABLE 3

Device Type Definition

```
<type
    name = "Raw EEG"
    type = "rawEEG"
    sync = "async"
    version = "1.0"
    developer = "Smith, John"
    schema = "rawEEGExten"
>
    <requirement name = "nodes" type - "int" indent - "yes"></requirement>
    <requirement name = "updateRate" type = "int"></requirement>
</type>
```

As mentioned above, the other plugin type developed for the presently disclosed architecture is the interface plugin, which functions similarly to the generic plugin. The main difference is that this plugin extends out a device. An example of an interface definition is provided in Table 4, below. This definition file behaves exactly the same as the plugin definition file but requires one extra tag, the interface tag. This tag defines the type of device being accessed, in this case the rawEEG type. Additionally, the interface can pass in any arguments defined as identifiers by the type. In this case, the interface is asking for a rawEEG device implementation which contains 14 nodes. It must also pass in the required receiver element, attributes, and implementation class for its receiver.

TABLE 4

Interface Definition

```
<plugin
    name = "Interpretor"
    id = "Interpretor.Interpretor"
    type - "interface"
    version = "1.0"
    developer = "Smith, John"
    <interface
        type = "rawEEG"
        nodes = "14">
```

TABLE 4-continued

Interface Definition

```
  <Receiver
    updateRate = "256"
    numNodes = "14"
    class = "interpretorRec">
  </Receiver>
</interface>
<extension-point id = "interpretor.interpretor.command" name = "command"
schema = command"/>
</plugin>
```

In addition to training as described above, the core program 160 within the architecture of the framework 100 is responsible for managing all of the plugins, devices, and types within the current implementation. It does so by scanning predefined folders for files of the expected type and format. It begins by scanning for device type implementations, then for device implementations. These devices are given a schema and any defined identifiers are assigned as keys to the possible devices within a type.

After all devices have been loaded, generic plugins and interfaces are scanned. Once these plugins are found, they are parsed and a schema object is generated for each of the extension points within the plugin. These schema objects will be used to ensure that plugins extending an extension point include the correct variables. Any plugin which extends an extension point is added to a list within that extension point for tracking. Additionally, the extension point is added to a list within the extending plugin to allow for two way communication. The core program manages all connections between the plugins by adding them to the relevant plugin and extension point lists based on the IDs provided within the definition file.

After all devices and plugins have been parsed, the run step begins. Each device's implemented run method is called with a new thread. This allows multiple devices to drive different sets of plugins. The lists created by the core program then allow for each of the devices to communicate with their interfaces, who communicate with their extending plugins and so on. The communication can be implemented as synchronous or asynchronous.

The following discussion describes how the disclosed framework 100 utilizing the plugin architecture operates in both the training mode and in the run mode.

Figure 3:
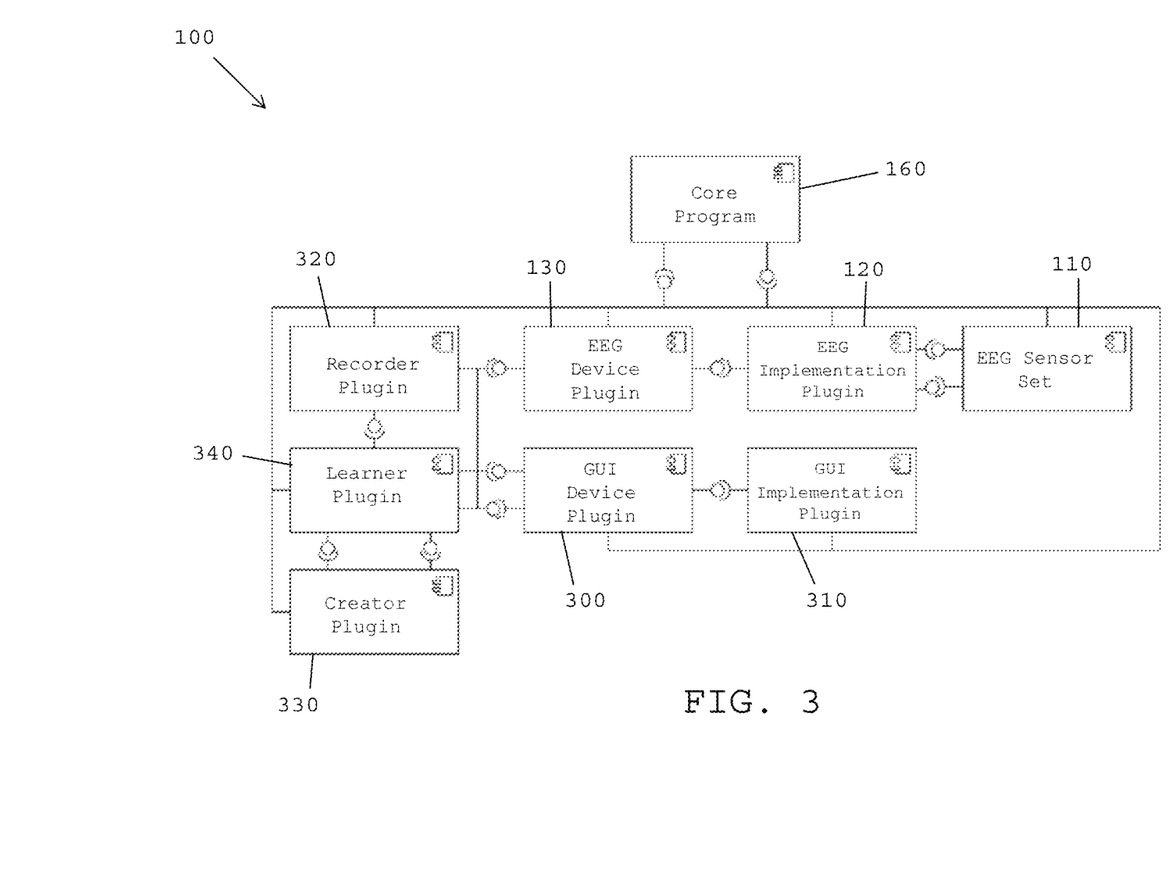
FIG. 3 depicts the extensible framework of FIG. 1 that includes the components for the training mode for learning commands, according to exemplary embodiments.

In the training mode, certain plugins were developed to interact with the framework 100. FIG. 3 depicts an embodiment of the framework 100 operating in the training mode. A first plugin created for use in the training mode is the GUI device 300 having a GUI type. This type creates a generic extension point for any device implementing this type. The GUI type includes the guiExten extension point with the following elements: guiBlock, Button, Entry, Text. The guiBlock will hold the Button, Entry, and Text elements. The entry element allows for user input to be processed, the text element allows for text to be placed, and the button element takes a class as an argument which will be called when the button is pressed.

The GUI implementation 310 of a training type utilized for this project is the training GUI. In the example described herein, the training GUI was created using TkInter, and the training GUI creates the GUI elements corresponding to any elements passed into it using its GUI extension point. Additionally, it assigns each extending plugin its own subsection of the training GUI with its name placed as a divider.

The EEG device 130 type includes a simple extension point which allows for interfaces to register themselves as receivers for the EEG device 130. It also includes an identifier, numNodes, which allows for an interface to request an EEG device 130 with the number of nodes if it is available. The extension point includes a generic extensionHandler method which will simply pass the received EEG signal to each of the registered extensions. This data should be formatted as a list of raw EEG values with all extra data removed.

The EEG device 130 implements the communication with the EEG sensor set 110. It begins by registering with the local app by passing it the credentials for login. It then subscribes to the raw EEG data stream and begins receiving data. Whenever this data is received, it passes it to the EEG extension point so that all extending plugins can access the raw data.

With respect to FIG. 3, the Recorder plugin 320 allows for the collection of raw EEG data into log files. In order to organize these logs, the GUI device type is used. The Recorder plugin 320 registers a GUI Block with two text and two entry fields as well as a button. The text fields are utilized to label the two entry fields. The first entry field contains the name of the model being trained. This name will be used to generate a unique folder for the log files. The second entry field contains the name of the command being recorded. When pressed, the button will generate data for 10 seconds, placing the collected raw EEG file into the folder defined by the first entry field with the name provided by the second entry field. If multiple recordings exist for a single command, a number will be appended to the recording name.

This plugin is also an interface for the EEG device 130. The Recorder plugin 320 listens to the raw EEG data extension point, but only processes and uses the data when a recording is taking place. During this time, the raw EEG data is simply placed into the defined text file. The Recorder plugin 320 also contains a single extension point which allows for other plugins to record data without utilizing the GUI.

In FIG. 3, the Creator plugin 330 is utilized for the conversion of raw EEG logs into power band data logs. This plugin contains a single extension point, fileParser, which allows for extending plugins to convert data themselves. This data conversion follows the process described in Algorithm 1 (above), and the output data is saved into separate log files for each command. In embodiments, the data takes the form of a csv file.

The Learner plugin 340 implements the machine learning portion of the project. The Learner plugin 340 interfaces with the GUI device 130 to allow for control utilizing the GUI device 300. One text field is used to label the one text entry field present. This entry field allows for the definition of a model name. This model name is the folder that the Learner plugin 340 checks for power band data. Finally, the GUI extension includes a button which will activate the training method, such as the training method described above. In embodiments, to verify the data, a quarter of the recordings are set aside for testing. The Learner plugin 340 then creates a model for the given data and outputs it into the provided folder.

The Learner plugin 340 extends the Creator plugin 330. If the data present within the model folder is formatted as raw EEG data, the Learner plugin 340 will utilize the Creator plugin 330 for data conversion. The Learner plugin 340 also includes its own extension point, learn, which allows for external plugins to provide a path which the learning algorithm should run on.

Returning to FIG. 1, the framework 100 in the run mode is depicted. The EEG device type includes a simple extension point which allows for interfaces to register themselves as receivers for the EEG device 130. It also includes an identifier, numNodes, which allows for an interface to request an EEG device 130 with the number of nodes if it is available. The extension point includes a generic extensionHandler method which will simply pass the received EEG signal to each of the registered extensions. This data should be formatted as a list of raw EEG values with all extra data removed.

The EEG device 130 implements the communication with the EEG sensor set 110 through the EEG implementation 120. The EEG device 130 begins by registering with the local application (i.e., EEG implementation 120) by passing the local application the credentials for login. The EEG implementation 120 then subscribes to the raw EEG data stream and begins receiving data. Whenever this data is received, it passes it to the EEG extension point so that all extending plugins can access the raw data.

The interpreter plugin 150 implements the categorization described in Algorithm 2, above. The Interpreter plugin 150 contains one extension point which allows for other plugins to register their desired commands with the interpreter. This plugin interfaces with the EEG device type and collects raw EEG data until 256 samples are collected for categorization. Once this takes place, the FFT data is passed to each extension's handler where the required machine learning model can determine the command that should be run. The extensions are then free to act on this categorization as needed.

The interpreter extension point includes two elements. The first element is the actionSet. This element contains a grouping of commands, each is assigned a number matching the index within the machine learning prediction matrix. By default, the command number whose index most closely matches the most recently received prediction matrix will be called. These commands are implemented with a commandAction element. The interpreter extension point allows for the creation of a custom actionSet class. In this case, the prediction matrix will instead be handled by the user defined class. If no user defined actionSet is used, an extending plugin must implement a commandAction class to define the behavior for each command.

In the example embodiment shown in FIG. 1, the framework 100 includes two example object control plugins 140, which are the lighting program for control of a light switch and the maze chase game discussed above. The example object control plugins 140 extend the interpreter plugin 150. The lighting program passes a model for use with two commands as well as a command to toggle lights. The interpreter plugin 150 can handle all of the logic and actions on categorization. The example object control plugin 140 lighting program itself only implements a method to be called when a command is activated. In the example embodiment, this method simply passes the command to toggle to the Raspberry Pi. To do so, the plugin extends the interpreter's extension point, passing the desired method into the commandAction element within the extension point.

The example maze chase game program allows for the control of a maze chase game simulator using a virtual joystick. The object control plugin 140 for this program extends the interpreter plugin 150 and provides a model for use with four commands (i.e., the four directional commands). To do so, the object control plugin 140 passes its own manager into the actionSet element within the interpreter plugin 150. Rather than relying on the default command handling, the object control plugin 140 for the maze chase game can now implement its own categorization methodology. The plugin waits for four categorizations to take place and then makes a prediction based upon the most common command sent during that time. This command is then passed to the corresponding virtual joystick command to allow for control of the virtual joystick.

In view of the foregoing, it has been demonstrated that the presently disclosed architecture allows an EEG device to be utilized to control real world objects. Further, the architecture is modifiable, usable by a variety of users/developers, and scalable. In particular, new plugins do not require knowledge of another plugin's implementation, and a new plugin can be added to the core functionality of the program without requiring user input. Indeed, to add a plugin to the system, the new plugin only needs to be added to the plugin folder. After this is complete, the plugin will automatically be added to the system. Further, a new plugin can add its own extension points as well as data format, which is accomplished through the .xml definition files laid out in the architecture as well as the python implementation files and extension point files. Advantageously, new devices and software can be added to the system through pre-developed plugins. In this way, a user or developer would not need to have an understanding of how a BCI works, and they would just need to incorporate a set of plugins that integrate the application into a BCI.

Thus, in the presently disclosed architectural implementation, a user is capable of controlling multiple digital and physical devices simultaneously with an EEG device. This device reads in brainwave data, and passes it to a machine learning algorithm which accurately categorizes commands. The implemented architecture allows for the extension of these core functionalities to include any new devices. This is accomplished through robust custom interface definitions provided herein.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for controlling objects using brainwaves, the system comprising:
    a first set of electroencephalogram (EEG) electrodes configured to be positioned on a head of a user and to collect EEG signals;
    one or more computer readable storage mediums comprising a framework configured to execute an extensible architecture through which EEG signals are interpreted for control of a first object, the framework comprising:
        a first EEG device plugin associated with the first set of EEG electrodes and configured to extract the EEG signals from the first set of EEG electrodes;
        an interpreter plugin configured to convert the EEG signals extracted by the first EEG device plugin into a first set of commands; and
        a first object control plugin configured to access the first set of commands through an extension point of the interpreter plugin and to execute the first set of commands to control the first object;
    wherein the extensible architecture is configured to extend to at least one further EEG device plugin associated with a different set of EEG electrodes and to at least one further object control plugin associated with at least one further set of commands and at least one further object.

2. The system of claim 1, wherein the interpreter plugin transforms the EEG signals from a time domain to brainwaves in a frequency domain using an FFT and wherein the brainwaves grouped in a plurality of bands for characterization of the first set of commands.

3. The system of claim 2, wherein the plurality of bands comprises a delta band including brainwaves at a frequency of 0.5 to 4 Hz, a theta band including brainwaves at a frequency of 5 to 8 Hz, an alpha band including brainwaves at a frequency of 9 to 14 Hz, a beta band including brainwaves at a frequency of 15 to 30 Hz, and a gamma band including brainwaves at a frequency above 30 Hz.

4. The system of claim 2, wherein a machine learning model is configured to match the brainwaves grouped in the plurality of bands to the first set of commands.

5. The system of claim 4, wherein the machine learning model comprises a neural network configured to recognize the first set of commands using deep learning over an input layer, one or more hidden layers, and an output layer.

6. The system of claim 1, wherein the framework comprises a training mode in which the first set of commands is learned from the EEG signals.

7. The system of claim 6, wherein the framework comprises a recorder plugin configured to collect the EEG signals into a log file.

8. The system of claim 7, wherein the framework comprises a creator plugin configured to convert the EEG signals collected in the recorder plugin into brainwaves grouped into a plurality of frequency bands.

9. The system of claim 8, wherein the framework comprises a learner plugin that extends the creator plugin and is configured to run a training method to learn the first set of commands.

10. The system of claim 9, wherein the framework further comprises a GUI plugin that interfaces with the learner plugin, the GUI plugin configured to allow a user to initiate the training method and to label the first set of commands.

11. The system of claim 9, wherein the learner plugin is configured to run the training method involving a machine learning model that analyzes (i) at least five logs of brainwaves of the user over at least ten seconds during which the user is not sending any of the first set of commands and (ii) at least five logs of brainwaves of the user over at least ten seconds during which the user is sending at least one of the first set of commands.

12. The system of claim 1, wherein the framework is configured to operate the first object control plugin and the at least one further object control plugin synchronously or asynchronously.

13. The system of claim 1, wherein the first EEG device plugin receives at least 128 samples per second of the EEG signals from the first set of EEG electrodes.

14. The system of claim 1, wherein the first EEG device plugin is configured to extract the EEG signals from the first set of EEG electrodes using a first EEG device implementation plugin that accesses the EEG signals through an application programming interface.

15. The system of claim 1, wherein the first set of EEG electrodes comprises from five to thirty-two electrodes incorporated into a headset configured to be worn on the head of the user.

* * * * *